US011690830B2

(12) United States Patent
Strupp

(10) Patent No.: US 11,690,830 B2
(45) Date of Patent: Jul. 4, 2023

(54) BETAHISTINE, OR A PHARMACEUTICALLY ACCEPTABLE SALT THEREOF, AND A MONOAMINE OXIDASE INHIBITOR, FOR USE IN THE TREATMENT OR PREVENTION OF ONE OR MORE SYMPTOMS OF VERTIGO IN A SUBJECT

(71) Applicant: INTRABIO LTD., London (GB)

(72) Inventor: Michael Strupp, Munich (DE)

(73) Assignee: IntraBio Ltd., London (GB)

( * ) Notice: Subject to any disclaimer, the term of this patent is extended or adjusted under 35 U.S.C. 154(b) by 26 days.

(21) Appl. No.: 17/396,064

(22) Filed: Aug. 6, 2021

(65) Prior Publication Data

US 2021/0361632 A1 Nov. 25, 2021

Related U.S. Application Data

(63) Continuation of application No. 16/499,087, filed as application No. PCT/GB2018/050822 on Mar. 28, 2018, now Pat. No. 11,083,718.

(30) Foreign Application Priority Data

Mar. 28, 2017 (GB) .................................. 1704949
Jul. 20, 2017 (GB) .................................. 1711677

(51) Int. Cl.
  *A61K 31/4402* (2006.01)
  *A61P 25/00* (2006.01)
  *A61K 9/00* (2006.01)
  *A61K 31/137* (2006.01)

(52) U.S. Cl.
  CPC ........ *A61K 31/4402* (2013.01); *A61K 9/0053* (2013.01); *A61K 31/137* (2013.01); *A61P 25/00* (2018.01)

(58) Field of Classification Search
  CPC .............. A61K 31/4402; A61K 31/137; A61K 9/0053; A61P 25/00
  See application file for complete search history.

(56) References Cited

U.S. PATENT DOCUMENTS

| 11,083,718 B2 | 8/2021 | Strupp |
| 2008/0004254 A1 | 1/2008 | Barak |

FOREIGN PATENT DOCUMENTS

| EP | 2491930 A1 | 8/2012 |
| WO | WO-2009143572 A1 | 12/2009 |
| WO | WO-2018178670 A1 | 10/2018 |

OTHER PUBLICATIONS

Leegwater-Kim, Clinical Interventions in Aging, vol. 5, 149-156, 2010. (Year: 2010).*

Adrian, C., et al., "Efficacy and Safety of Betahistine Treatment in Patients With Meniere's Disease: Primary Results of a Long Term, Multicentre, Double Blind, Randomised, Placebo Controlled, Dose Defining Trial (Bemed Trial)," British Medical Association 352:h6816, British Medical Association, England (2016).
Ahsan, S.F., et al., "Systematic Review and Meta-Analysis of Meniett Therapy for Meniere's Disease," The Laryngoscope 125(1):203-208, Wiley-Blackwell, United States (Jan. 2015).
Alexander, T.H. and Harris, J.P., "Current Epidemiology of Meniere's Syndrome," Otolaryngologic clinics of North America 43:965-970, WB Saunders, Philadelphia (Oct. 2010).
Anonymous, "Betahistin Stada Fachinformation," accessed at http://fachinformation.srz.de/pdf/stadapharm/betahistinstada6mg12mgtabletten.pdf, XP055484892 (Jan. 2014).
Anonymous, "Committee on Hearing and Equilibrium guidelines for the diagnosis and evaluation of therapy in Menière's disease. American Academy of Otolaryngology—Head and Neck Foundation, Inc," Otolaryngology Head and Neck surgery 113(3):181-185, Sage Publications, England (Sep. 1995).
Anonymous, "Drugs & Biologies Search Results: Phenylephrine hydrochloride," accessed at https://integrity.thomsonpharma.com/integrity/xmlxsl/pk_prod_list.xml_prod_list_card_pr?p_id=70250&p_tsearch=A, accessed on Jun. 15, 2018, XP055484739 (Jan. 2018).
Anonymous, "Drugs & Biologies Search Results: Betahistine dihydrochloride," accessed at https://integrity.thomson-pharma.com/integrity/xmlxsl/pk_qcksrch.show_records?sessioniD=1&history=&query=betahistin*&abbreviation=PRO&language=en, accessed on Jun. 15, 2018, XP055484929 (Jan. 2018).
Berge, S.M., et al., "Pharmaceutical Salts," Journal of Pharmaceutical Sciences 66(1):1-19, Wiley, United States (Jan. 1977).
Bertlich, M., et al., "Betahistine Metabolites, Aminoethylpyridine, and Hydroxyethylpyridine Increase Cochlear Blood Flow in Guinea Pigs in Vivo," International Journal of Audiology 53(10):753-759, BC Decker, England (Oct. 2014).
Bertlich, M., et al., "Histaminergic H3-Heteroreceptors as a Potential Mediator of Betahistine-Induced Increase in Cochlear Blood Flow," Audiology & neuro-otology 20(5):283-293, Karger, Switzerland (2015).
Bisdorff, A., et al., "Classification of Vestibular Symptoms: Towards an International Classification of Vestibular Disorders," Journal of vestibular research 19(1-2):1-13, Pergamon Press, Netherland (2009).
Braga, C.A., et al., "The Anti-parkinsonian Drug Selegiline Delays the Nucleation Phase of alpha-synuclein Aggregation Leading to the Formation of Nontoxic Species," Journal of Molecular Biology 405(1):254-273, Academic Press, England (Jan. 2011).
Chen, X.Y., et al., "LC-MS-MS Analysis of 2-pyridylacetic Acid, a Major Metabolite of Betahistine: Application to a Pharmacokinetic Study in Healthy Volunteers," Xenobiotica 33(12):1261-1271, Taylor & Francis, England (Dec. 2003).

(Continued)

*Primary Examiner* — D Margaret M Seaman
(74) *Attorney, Agent, or Firm* — Sterne, Kessler, Goldstein & Fox P.L.L.C.

(57) ABSTRACT

A first aspect of the invention relates to betahistine, or a pharmaceutically acceptable salt thereof, and a monoamine oxidase inhibitor, for use in the treatment or prevention of one or more symptoms of vertigo in a subject.
A second aspect of the invention relates to a method of treating or preventing one or more symptoms of vertigo in a subject, said method comprising administering to the subject (i) betahistine, or a pharmaceutically acceptable salt thereof, and (ii) a monoamine oxidase inhibitor.

20 Claims, 1 Drawing Sheet

(56) References Cited

OTHER PUBLICATIONS

Cutler, A.R., et al., "Two-handed Endoscopic-Directed Vestibular Nerve Sectioning: Case Series and Review of the Literature," Journal of Neurosurgery 117(3):507-513, American Association of Neurological Surgeons, United States (Sep. 2012).

Dezsi, L. and Vecsei, L., "Monoamine Oxidase B Inhibitors in Parkinson's Disease," CNS & neurological disorders drug targets 16(4):425-439, Bentham Science Publishers, United Arab Emirates (2017).

Elsworth, J.D., et al., "Deprenyl Administration in Man: a Selective Monoamine Oxidase B Inhibitor Without the 'cheese Effect," Psychopharmacology 57(1):33-38, Springer Nature, Switzerland (Jan. 1978).

Emea, "Committee for Medicinal Products for Human Use: Guideline on Clinical Investigation of Medicinal Products for the Treatment of Migraine," Doc. Ref. CPMP/EWP/788/01 Rev. 1, European Medicines Agency, Jan. 2007.

Escamez, J.A.L., et al., "Diagnostic Criteria for Meniere's Disease," Journal of Vestibular Research 25(1):1-7, Pergamon Press, Netherland (2015).

Fisher, L.M., et al., "Oral Steroid Treatment for Hearing Improvement in Meniere's Disease and Endolymphatic Hydrops," Otology & Neurotology 33:1685-1691, Lippincott Williams & Wilkins, United States (Dec. 2012).

Goto, F., et al., "Lateral Semicircular Canal Plugging With Endolymphatic Sac Decompression as New Surgical Treatment for Intractable Meniere's Disease," Acta Oto-laryngologica 132(8):893-895, Scandinavian University Press, England (Aug. 2012).

Gurkov, R., et al., "In Vivo Visualization of Endolyphatic Hydrops in Patients With Meniere's Disease: Correlation With Audiovestibular Function," European Archives of Oto-rhino-laryngology 268(12):1743-8, Springer International, Germany (Dec. 2011).

Gurkov, R., et al., "Effect of Transtympanic Low-Pressure Therapy in Patients With Unilateral Meniere's Disease Unresponsive to Betahistine: A Randomised, Placebo-Controlled, Double-Blinded, Clinical Trial," The Journal of Laryngology and Otology 126(4):356-362, Cambridge University Press, England (Apr. 2012).

Hallpike, C.S. and Cairns, H., "Observations on the Pathology of Ménière's Syndrome: (Section of Otology)," Proceedings of the Royal Society of Medicine 31(11):1317-1336, Royal Society of Medicine, England (Sep. 1938).

Harcourt, J. and Cosentino, S., "Betahistine for Meniere's Disease," British Medical Association 352:i46, British Medical Association, England (2016).

Harcourt, J., et al., "Meniere's Disease," British Medical Association 349:g6544, British Medical Association, England (Nov. 2014).

Harner, S.G., et al., "Long-term Follow-Up of Transtympanic Gentamicin for Meniere's Syndrome," Otology & Neurotology 22(2):210-214, Lippincott Williams & Wilkins, United States (Mar. 2001).

Harris, J.P., et al., "Current-day Prevalence of Meniere's Syndrome," Audiology & Neuro-otology 15:318-322, Basel, Switzerland (2010).

Huang, T.S., et al., "Endolymphatic Sac Surgery for Meniere's Disease: Experience With Over 3000 Cases," Otolaryngologic clinics of North America 35(3):591-606, Saunders, United states (Jun. 2002).

Ihler, F., et al., Betahistine Exerts a Dose-Dependent Effect on Cochlear Stria Vascularis Blood Flow in Guinea Pigs In Vivo, PLoS ONE 7(6):e39086, Public Library of Science, United states (2012).

International Search Report and Written opinion for International Application No. PCT/GB2018/050822, dated Jun. 26, 2018, 14 pages.

James, A.L. and Burton, M.J., "Betahistine for Meniere's Disease or Syndrome," The Cochrane Database of Systematic Reviews 1:CD001873 Wiley, England (2001).

Lacour, M., "Betahistine Treatment in Managing Vertigo and Improving Vestibular Compensation: Clarification," Journal of Vestibular Research 23(3):139-151, Pergamon Press, Netherland (2013).

Laurikainen, E., et al., "The Vascular Mechanism of Action of Betahistine in the Inner Ear of the Guinea Pig," European archives of oto-rhino-laryngology 255(3):119-123, Springer International, Germany (1998).

Lezius, F., et al., "High-dosage Betahistine Dihydrochloride Between 288 and 480 Mg/Day in Patients With Severe Meniere's Disease: A Case Series," European Archives of Oto-rhino-laryngology 268(8):1237-1240, Springer International, Germany (Aug. 2011).

Melnikov, O.A., et al., "Betahistine plus piracetam dual therapy versus betahistine monotherapy for peripheral vestibular vertigo: A confounder-corrected subanalysis of the OSVaLD study," Current Medical Research and Opinion 31(11):1951-1962, Informa Healthcare, England (Nov. 2015).

Minor, L.B., et al., "Meniere's Disease," Current Opinion in Neourology 17(1):9-16, Current Science, England (Feb. 2004).

Mira, E., et al., "Betahistine Dihydrochloride in the Treatment of Peripheral Vestibular Vertigo," European Archives of Oto-rhino-laryngology 260(2):73-77, Springer International, Germany (Feb. 2003).

Murdin, L., et al., "Betahistine for Symptoms of Vertigo," Cochrane database of systematic reviews 6:CD010696, Wiley, England (Jun. 2016).

Nauta, J.J., et al., "Meta-analysis of Clinical Studies With Betahistine in Meniere's Disease and Vestibular Vertigo," European Archives of Oto-rhino-laryngology 271(5):887-897, Springer International, Germany (May 2014).

NDA 20-647/S-006 and S-007: Eldepryl (Selegiline hydrochloride) Capsules, accessed at https://www.accessdata.fda.gov/drugsatfda_docs/label/2008/020647s006s0071bl.pdf, 2008, 11 pages.

Paparella, M.M., "Vestibular Meniere's Disease," Otolaryngology Head and Neck surgery 93(2):148-151, The Academy, England (Apr. 1985).

Park, J.J., et al., "Meniere's Disease and Middle Ear Pressure: Vestibular Function After Transtympanic Tube Placement," Acta oto-laryngologica 129(12):1408-1413, Scandinavian University Press, England (Dec. 2009).

Philips, J.S. and Westerberg, B., "Intratympanic Steroids for Meniere's Disease or Syndrome," Cochrane database of systematic reviews 7:CD008514, Wiley, England (Jul. 2011).

Pullens, B. and Benthem, P.P.V., "Intratympanic Gentamicin for Meniere's Disease or Syndrome," Cochrane Database of Systematic Reviews (Mar. 2011).

Pullens, B., et al., "Surgery for Meniere's Disease," The Cochrane database of systematic reviews 2:CD005395, Wiley, England (Feb. 2013).

Singh, N., et al., "In Vitro Effects of Cognitives and Nootropics on Mitochondrial Respiration and Monoamine Oxidase Activity," Molecular Neurobiology 54(8):5894-5904, Humana Press, United States (Oct. 2017).

Smith, W.K., et al., "A National Survey Amongst UK Otolaryngologists Regarding the Treatment of Meniere's Disease," The Journal of Laryngology and Otology 119(2):102-105, Headley Brothers, England (Feb. 2005).

Sternson, L.A., et al., "The Metabolism of Betahistine in the Rat," Drug Metabolism & Disposition, 2(2):123-128, American Society for Pharmacology and Experimental Therapeutics, United States (Mar.-Apr. 1974).

Strupp, M. and Brandt, T., "Peripheral Vestibular Disorders," Current Opinion in Neurology 26(1):81-89, Current Science, England (Feb. 2013).

Strupp, M., et al., "Long-term Prophylactic Treatment of Attacks of Vertigo in Meniere's Disease-Comparison of a High With a Low Dosage of Betahistine in an Open Trial," Acta Oto-laryngologica 128(5):520-524, Scandinavian University Press, England (May 2008).

Strupp, M., et al., "Meniere's Disease: Combined Pharmacotherapy With Betahistine and the MAO-B Inhibitor Selegiline—An Observational Study," Journal of Neurology 265(1):80-85, Springer, Germany (Oct. 2018).

(56) References Cited

OTHER PUBLICATIONS

Strupp, M. and Magnusson, M., "Acute Unilateral Vestibulopathy," Neurologic clinics 33(3):669-685, Saunders, United States (Aug. 2015).

Teufert, K.B. and Doherty, J., "Endolymphatic Sac Shunt, Labyrinthectomy, and Vestibular Nerve Section in Meniere's Disease," Otolaryngologic Clinics of North America 43(5):1091-1111, Saunders, United States (Oct. 2010).

Thirlwall, A.S. and Kundu, S., "Diuretics for Meniere's Disease or Syndrome," Cochrane Database of Systematic Reviews 3: CD003599, Wiley, England (Jul. 2006).

Van Sonsbeek, S., et al., "Positive Pressure Therapy for Meniere's Disease or Syndrome," The Cochrane Database of Systematic Reviews 3:CD008419, Wiley, England (Mar. 2015).

Wang, S.J., et al., "The Clinical Benefit of Device Therapy for Meniere's Disease in Adults: Systematic Review and Meta-Analysis," The Journal of International Advanced Otology 15(1):121-129, Mediterranean Society of Otology and Audiology, Turkey (Apr. 2019).

Wasson, J., et al., "Intratympanic Gentamicin Treatment for Unilateral Meniere's Disease: Long-Term Follow Up of a Proven Regime," The Journal of laryngology and otology 127:20-24, Headley Brothers, England (Jan. 2013).

Watanabe, Y., et al., "Intermittent Pressure Therapy of Intractable Meniere's Disease and Delayed Endolymphatic Hydrops Using the Transtympanic Membrane Massage Device: A Preliminary Report," Acta Oto-laryngologica 131:1178-1186, Scandinavian University Press, England (Nov. 2011).

Westhofen, M., "Meniere's Disease: Evidence and Controversies," HNO 57(5):446-454, Springer Verlag, Germany (May 2009).

Wladislavosky-Waserman P., et al., "Meniere's Disease: A 30-year Epidemiologic and Clinical Study in Rochester, MN, 1951-1980," Laryngoscope 94(8):1098-1102, Wiley-Blackwell, United States (Aug. 1984).

Yu, M.S., et al., "Long-term Results of Endolymphatic Mastoid Shunt Surgery in Patients With Intractable Meniere's Disease," Otolaryngology Head and Neck Surgery 141(2):237-242, The Academy, England (Aug. 2009).

\* cited by examiner

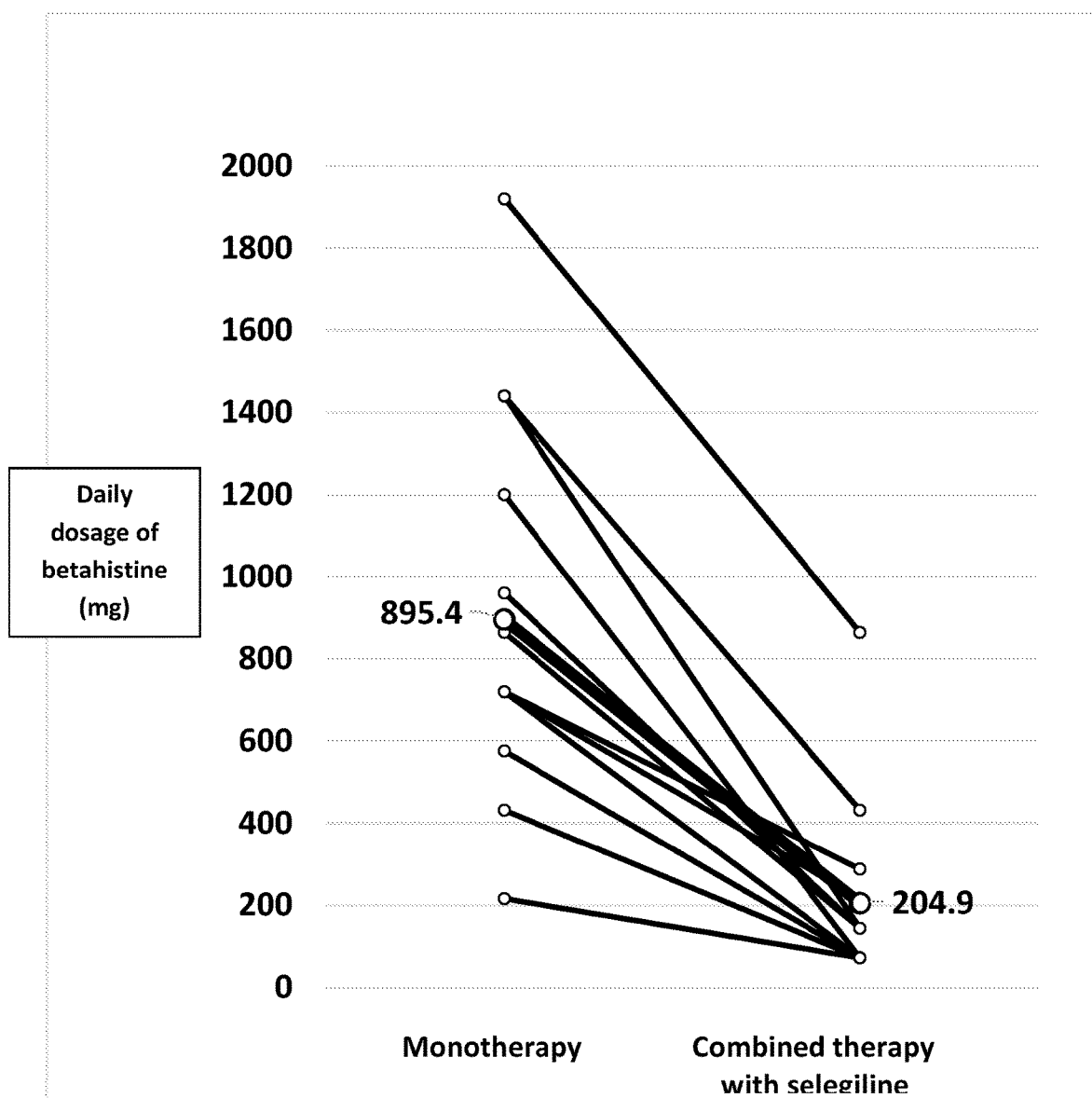

BETAHISTINE, OR A PHARMACEUTICALLY ACCEPTABLE SALT THEREOF, AND A MONOAMINE OXIDASE INHIBITOR, FOR USE IN THE TREATMENT OR PREVENTION OF ONE OR MORE SYMPTOMS OF VERTIGO IN A SUBJECT

FIELD OF THE INVENTION

The present invention relates to combination therapy for the treatment or prevention of one or more symptoms of vertigo.

BACKGROUND TO THE INVENTION

Vertigo is a commonly experienced symptom in which individuals experience a false sensation of movement. Vertigo is a specific subtype of dizziness thought to originate in the inner ear labyrinth or its neural connections. Dizziness is a term that is commonly used by patients to describe various sensations of light headedness, imbalance, illusory feelings of movement or disorientation. There are three types of vertigo: peripheral, central and functional, depending on the cause.

Vertigo is defined by the Bárány Society (The International Balance Disorders Association) as "the sensation of self-motion when no self-motion is occurring or the sensation of distorted self-motion during an otherwise normal head movement" [46]. It may be a sensation of rotation (spinning vertigo), or may be a different sensation of self motion (non-spinning vertigo). Peripheral vertigo is commonly caused by problems with the inner ear and can in this context be referred to as vestibular vertigo.

The symptoms of vertigo are variable. In some cases symptoms may be mild, whilst in others there may be a single short-lived episode. Frequently, however, symptoms become prolonged, or individuals become prone to recurrent attacks. Importantly, vertigo increases the risk of falls, which is a major public health problem in the elderly. Vertigo is a subjective experience and its measurement is dependent on the account of the individual experiencing it.

Peripheral vertigo has many causes including vestibular disorders such as Menière's disease, vestibular neuritis and benign paroxysmal positional vertigo, each of which can be diagnosed by standardized criteria.

Menière's disease is characterised by recurrent attacks of vertigo, fluctuating sensorineural hearing loss, aural fullness and tinnitus [1]. Its histopathological hallmark is endolymphatic hydrops [2,3]. Lifetime prevalence of the disease in the United States is reported as 190 per 100 000 people, with a ratio of 1.89 women to every man [4,5]. Annual incidence of the disease in the USA was 15.3 per 100 000 people (age adjusted rate) [6]. The peak age of onset is during the fifth and sixth decade [7]. For patients with Menière's disease, unpredictable vertigo attacks are the most important and unpleasant symptom.

Many therapeutic approaches to Menière's disease have been studied. These include a low salt diet and diuretics [8], oral and intratympanic steroid application [9,10] or minimal invasive interventions (such as insertion of a ventilation tube into the tympanic membrane [11,12], endolymphatic sac surgery [13], or pulsed low pressure delivery (using Meniett devices)) [14-17]. For patients who do not respond to these treatments, more aggressive procedures can be considered, such as intratympanic application of gentamycin [18,19], plugging of the semicircular canal, labyrinthectomy, or neurectomy [20-23]. However, these interventions are irreversible and could damage the cochlear and vestibular organ. Furthermore, a recent review showed there was no evidence of any benefit in a surgical approach [24,25].

Betahistine is a licensed drug for Menière's disease-like symptom complexes, which contains the active ingredient betahistine dihydrochloride (maximum daily dose 48 mg) or betahistine dimesylate (maximum daily dose 36 mg). Betahistine is a strong H3 antagonist and a weak H1 agonist [26] with three sites of action. Firstly, it increases dose-dependent cochlear blood flow [27], mainly via the H3 receptor as an inverse agonist [28]. Because betahistine has a strong first pass effect and is metabolised in the liver into three metabolites, not only betahistine but also its major metabolite aminoethylpyridine increases cochlear blood flow [29]. Secondly, betahistine increases histamine turnover in the central nervous and vestibular system, also mainly via the H3 receptor. Thirdly, it decreases vestibular input in the peripheral vestibular system, with possible involvement with the H3 and H4 receptors.

How betahistine might have an effect in the prophylactic treatment of Menière's disease is so far unknown. It could lead to an improvement of labyrinthine microcirculation, thereby rebalancing the production and resorption of endolymph. The drug was first registered in Europe in the 1970s and has been administered to more than 100 million patients so far. In Germany, UK and most other European countries, betahistine is the first line treatment for Menière's disease in clinical practice, before consideration of endolymphatic sac surgery or ablative gentamicin treatment [30]. The drug is inexpensive and well tolerated, and is one of the most frequently prescribed drugs for Menière's disease in Europe [31,32].

Despite its widespread use in Europe, betahistine is not approved by the US Food and Drug Administration, and observational studies or low quality randomised controlled trials of low and moderate betahistine doses have produced contradictory results on treatment efficacy. Several clinical studies assessing the effect of betahistine on the vestibular system and, to a lesser degree, audiological symptoms suggested that the drug improved these symptoms [33, 34]. However, according to a Cochrane systematic review of betahistine for Menière's disease or syndrome, there is insufficient evidence to indicate whether betahistine has any effect in currently approved dosages [33]. A more recent Cochrane review evaluated the effect of betahistine on the symptoms of vertigo [45]. Whilst there may be a positive effect in terms of reduction in vertigo symptoms, there was significant variability in the results and the quality of data was adjudged to be low. Moreover, there was insufficient information about the effect of betahistine on objective tests of inner ear balance organ function, and no information on the effect of betahistine on overall quality of life or falls. Until recently, randomised controlled trials that meet high quality standards were lacking, either due to inadequate diagnostic criteria or methods [35], or because the effect of betahistine treatment on vertigo was inadequately assessed.

The dose of betahistine in these earlier studies varied between 16 and 72 mg per day, which could explain the differences in symptom relief observed. Even higher doses of up to 480 mg per day have shown benefit for severe cases in a small case series, suggesting a possible effect of high dose regimens in the treatment of Menière's disease [37]. The drug seems to retain a good tolerability profile [33,45]. On the basis of many years' clinical experience, the dose was successively increased to 48 mg three times a day, pointing towards the role of long term treatment (up to 12 months). This dose increase was supported by an open, uncontrolled, non-masked study without a placebo arm that compared a high dose regimen of 48 mg three times daily with the recommended standard dose of 16 or 24 mg three times daily [36]. This non-interventional study showed that the higher dose was superior to the lower dose, and that the treatment effect of betahistine on the incidence of attacks of vertigo became more prominent over time.

More recently, a multicentre, double blind, randomised, placebo controlled, phase III superiority trial was undertaken to assess the long term prophylactic effects of betahistine dihydrochloride in two different doses and placebo [39]. The doses and placebo were administered continuously for nine months, and effects observed on the frequency, duration, and severity of acute attacks caused by Menière's disease, vertigo related impairment of quality of life, and vestibular and audiological function. The trial also aimed to ascertain the speed of effect—that is, whether the two active doses can be distinguished from each other or from placebo by how quickly reduction in attack frequency is achieved [38]. The results of the study indicated there was no difference between the three treatment groups (placebo, low dose and high dose betahistine), i.e. long term prophylactic treatment with betahistine dihydrochloride (at daily doses 2×24 mg or 3×48 mg) does not change the time course of vertigo episodes related to Menière's disease compared with placebo. Placebo intervention as well as betahistine treatment showed the same reduction of attack rates over the study's nine month treatment period.

In the light of the shortcomings of these studies, there is still an unmet need for new therapeutic treatments for the symptoms of vertigo, including those associated with Menière's disease. Indeed, this was confirmed in a recent Editorial article in the British Medical Journal (2016), where it was noted that the use of betahistine in treating Menière's disease is ineffective, and that patients urgently need better alternatives [40].

The present invention seeks to address this need by providing a new therapeutic approach which comprises administering betahistine in combination with a second active agent, namely, a monoamine oxidase inhibitor, for example, selegiline.

STATEMENT OF INVENTION

In a broad aspect, the present invention relates to a combination comprising betahistine, or a pharmaceutically acceptable salt thereof, and a monoamine oxidase inhibitor, and therapeutic uses thereof. Preferred embodiments are set out below and apply to all aspects as set out herein.

In a first aspect, the invention relates to betahistine, or a pharmaceutically acceptable salt thereof, and a monoamine oxidase inhibitor, for use in the treatment or prevention of one or more symptoms of vertigo in a subject.

Advantageously, the applicants have shown that administering betahistine, or a pharmaceutically acceptable salt thereof, in combination with a monoamine oxidase inhibitor such as selegiline surprisingly leads to an improved clinical outcome compared to patients receiving betahistine alone, for example, in terms of the number of vertigo attacks experienced. Selegiline is a monoamine oxidase (MAO) inhibitor approved for the treatment of Parkinson's disease, alone or in combination with levodopa. To date, selegiline has not been disclosed as being therapeutically effective in the treatment of Menière's disease or other peripheral vestibular diseases, either alone or in combination with any other active agent.

The presently claimed combination treatment is unexpected given that previous clinical studies on betahistine monotherapy have been inconclusive, and more recent reports have suggested that neither low doses nor high doses of betahistine are in fact clinically effective [39,40]. The administration of betahistine in combination with a monoamine oxidase inhibitor such as selegiline is able to achieve therapeutic efficacy with substantially lower doses of betahistine than reported for betahistine monotherapy. This is reflected by a dramatic reduction in the number of betahistine tablets required per day. By way of illustration, treatment with betahistine alone may require anything from 40 to 80 tablets each day (24 mg per tablet), and even then, may still not achieve a satisfactory therapeutic outcome for the patient. In contrast, when betahistine is administered in combination with selegiline, the number of betahistine tablets can be drastically reduced, for example, to as few as 3 to 12 tablets per day, or even 3 to 6 tablets per day.

A second aspect of the invention provides a combination comprising (i) betahistine, or a pharmaceutically acceptable salt thereof, and (ii) a monoamine oxidase inhibitor, for use in treating or preventing one or more symptoms of vertigo in a subject.

A third aspect of the invention relates to the use of (i) betahistine, or a pharmaceutically acceptable salt thereof, and (ii) a monoamine oxidase inhibitor, in the preparation of a medicament for the treatment or prevention of one or more symptoms of vertigo.

A fourth aspect of the invention relates to the use of a monoamine oxidase inhibitor, in the preparation of a medicament for the treatment or prevention of one or more symptoms of vertigo, wherein said medicament is for use in combination therapy with betahistine, or a pharmaceutically acceptable salt thereof.

A fifth aspect of the invention relates to the use of betahistine, or a pharmaceutically acceptable salt thereof, in the preparation of a medicament for the treatment or prevention of one or more symptoms of vertigo, wherein said medicament is for use in combination therapy with a monoamine oxidase inhibitor.

A sixth aspect of the invention relates to the use of betahistine, or a pharmaceutically acceptable salt thereof, in the preparation of a medicament for the treatment or prevention of one or more symptoms of vertigo, wherein said treatment comprises administering to a subject simultaneously, sequentially or separately a monoamine oxidase inhibitor, and betahistine, or a pharmaceutically acceptable salt thereof.

A seventh aspect of the invention relates to the use of a monoamine oxidase inhibitor, in the preparation of a medicament for the treatment or prevention of one or more symptoms of vertigo, wherein said treatment comprises administering to a subject simultaneously, sequentially or separately betahistine, or a pharmaceutically acceptable salt thereof, and a monoamine oxidase inhibitor.

An eighth aspect relates to betahistine, or a pharmaceutically acceptable salt thereof, and a monoamine oxidase inhibitor, as a combined preparation for simultaneous, sequential or separate use in treating or preventing one or more symptoms of vertigo.

A ninth aspect of the invention relates to a method of treating or preventing one or more symptoms of vertigo in a subject, said method comprising administering to the subject (i) betahistine, or a pharmaceutically acceptable salt thereof, and (ii) a monoamine oxidase inhibitor.

DETAILED DESCRIPTION

As mentioned above, one aspect of the invention relates to betahistine, or a pharmaceutically acceptable salt thereof, and a monoamine oxidase inhibitor, for use in combination therapy in the treatment or prevention of one or more symptoms of vertigo in a subject.

Administering the betahistine in combination with a monoamine oxidase inhibitor such as selegiline surprisingly renders the betahistine therapeutically useful in the treatment of peripheral vertigo, for example, in treating Menière's disease.

Preferably, the subject is a mammal, more preferably, a human.

As used herein, "treatment or prevention" includes preventing or alleviating one or more symptoms of vertigo. Symptoms of vertigo include, but are not limited to, false sensation of movement, dizziness, light headedness, imbalance and illusory feelings of movement or disorientation.

In one preferred embodiment, the invention relates to treating one or more symptoms of vertigo in a subject.

In another preferred embodiment, the invention relates to preventing one or more symptoms of vertigo in a subject.

In one preferred embodiment, the combination therapy reduces the frequency and/or severity of one or more symptoms of vertigo. In one highly preferred embodiment, the combination therapy reduces the frequency and/or severity of vertigo attacks experienced by the subject.

In one preferred embodiment, the vertigo is peripheral vertigo. Peripheral vertigo is commonly caused by problems with the inner ear, which controls balance.

In another preferred embodiment, the vertigo is central vertigo. Central vertigo is vertigo due to a disease originating from the central nervous system (CNS). Individuals with vertigo experience hallucinations of motion of their surroundings. Central vertigo may be caused by hemorrhagic or ischemic insults to the cerebellum, the vestibular nuclei, and their connections within the brain stem. Other causes include CNS tumors, infection, trauma, and multiple sclerosis.

In one preferred embodiment, the peripheral vertigo is acute vertigo. Preferably, the treatment reduces the symptoms of acute central vertigo and improves central compensation.

The effect of drug combinations is inherently unpredictable and there is often a propensity for one drug to partially or completely inhibit the effects of the other. The present invention is based on the surprising observation that administering behistine, or a pharmaceutically acceptable salt thereof, in combination, either simultaneously, separately or sequentially, with selegiline, or a pharmaceutically acceptable salt thereof, does not lead to any adverse interaction between the two agents. The unexpected absence of any such antagonistic interaction is critical for clinical applications.

In a preferred embodiment, the combination of betahistine, or a pharmaceutically acceptable salt thereof, and monoamine oxidase inhibitor produces an enhanced effect as compared to either drug administered alone. The surprising nature of this observation is in contrast to that expected on the basis of the prior art, and in particular, the observed lack of efficacy and contradictory clinical reports in relation to betahistine monotherapy. Without wishing to be bound by theory, it is believed that selegiline, which is an MAO inhibitor, reduces the first pass effect and leads to an increase in the blood concentration of betahistine.

The preferred embodiments as set out below are applicable to all the above-mentioned aspects of the invention.

In one preferred embodiment, the peripheral vertigo is caused by, or associated with, Menière's disease. Thus, in one embodiment, the combination is for use in treating Menière's disease.

Menière's disease is characterised by recurrent attacks of vertigo, fluctuating sensorineural hearing loss, aural fullness and tinnitus [1]. The Bárány Society and international collaborating organisations have recently published consensus clinical criteria for Menière's disease [49], taking forward the previously widely used American criteria [50].

One preferred embodiment of the invention relates to betahistine, or a pharmaceutically acceptable salt thereof, and a monoamine oxidase inhibitor, for use in the treatment of Menière's disease. Preferably, the treatment reduces or prevents the number of peripheral vertigo attacks in a subject suffering from Menière's disease.

Another preferred embodiment of the invention relates to betahistine, or a pharmaceutically acceptable salt thereof, and selginine or a pharmaceutically acceptable salt thereof, for use in the treatment of Menière's disease.

As used herein, "treatment of Menière's disease" includes preventing or alleviating one or more symptoms of the disease, which symptoms include vertigo, fluctuating sensorineural hearing loss, aural fullness and tinnitus. In one preferred embodiment, the combination therapy reduces the frequency and/or severity of one or more symptoms of the disease. In one highly preferred embodiment, the combination therapy reduces the frequency and/or severity of Menière's attacks experienced by the subject.

In another preferred embodiment, peripheral vertigo is caused by, or associated with, vestibular neuritis, also called vestibular neuronitis or nowadays acute unilateral peripheral vestibulopathy. One preferred embodiment of the invention thus relates to betahistine, or a pharmaceutically acceptable salt thereof, and a monoamine oxidase inhibitor, for use in the treatment of vestibular neuritis. Vestibular neuritis is characterized by an acute onset of severe spinning vertigo, postural imbalance, nausea and often vomiting. Clinical examination reveals a peripheral vestibular spontaneous nystagmus and a pathological head impulse test and Romberg test. It is assumed to be caused in most patients by the reactivation of an Herpes simplex virus type 1 infection [50].

Similar signs and symptoms can also be caused by a trauma to the vestibular nerve or labyrinth (concussion), by an ischemia of the labyrinth or an inflammation of the ear by Herpes zoster virus or bacteria. The same symptoms can also occur in patients with brainstem or cerebellar infarction ("vestibular pseudoneuritis").

In another preferred embodiment, the peripheral vertigo is caused by, or associated with, benign paroxysmal positional vertigo (BPPV). One preferred embodiment of the invention thus relates to betahistine, or a pharmaceutically acceptable salt thereof, and a monoamine oxidase inhibitor, for use in the treatment of BPPV. Benign paroxysmal positional vertigo develops when small crystals of calcium carbonate break free and find their way to the semicircular canal in the inner ear. This causes the brain to receive confusing messages about the body's position. Benign paroxysmal positional vertigo is diagnosed according to clinical criteria, as is vestibular neuritis [48].

In another preferred embodiment, the peripheral vertigo is caused by, or associated with, labyrinthitus. One preferred embodiment of the invention thus relates to betahistine, or a pharmaceutically acceptable salt thereof, and a monoamine oxidase inhibitor, for use in the treatment of labyrinthitus. Labyrinthitis is swelling and inflammation of the labyrinth, part of the inner ear that helps control balance. Labyrinthitis can occur after a viral infection or, more rarely, after an infection caused by bacteria.

As used herein the phrase "preparation of a medicament" includes the use of the components of the invention directly as the medicament in addition to their use in any stage of the preparation of such a medicament.

As used herein, the term "combination therapy" refers to therapy in which the betahistine, or pharmaceutically acceptable salt thereof, and the monoamine oxidase inhibitor, are administered if not simultaneously, then sequentially within a timeframe, that they both are available to act therapeutically within the same time-frame.

The betahistine, or a pharmaceutically acceptable salt thereof, and monoamine oxidase inhibitor, may be administered simultaneously, in combination, sequentially or separately (as part of a dosing regime).

As used herein, "simultaneously" is used to mean that the two agents are administered concurrently, whereas the term "in combination" is used to mean they are administered, if not simultaneously, then "sequentially" within a timeframe that they both are available to act therapeutically within the same time-frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction therebetween, and their respective half-lives.

In contrast to "in combination" or "sequentially", "separately" is used herein to mean that the gap between administering one agent and the other is significant i.e. the first administered agent may no longer be present in the bloodstream in a therapeutically effective amount when the second agent is administered.

In one preferred embodiment of the invention, the betahistine is administered sequentially or separately prior to the monoamine oxidase inhibitor.

In another particularly preferred embodiment, the monoamine oxidase inhibitor is administered sequentially or separately prior to the betahistine.

In one preferred embodiment, the betahistine and monoamine oxidase inhibitor are each administered in a therapeutically effective amount with respect to the individual components; in other words, the betahistine and monoamine oxidase inhibitor are administered in amounts that would be therapeutically effective even if the components were administered other than in combination.

In another preferred embodiment, the betahistine and monoamine oxidase inhibitor are each administered in a sub-therapeutic amount with respect to the individual components; in other words, the betahistine and monoamine oxidase inhibitor are administered in amounts that would be therapeutically ineffective if the components were administered other than in combination.

In one preferred embodiment, the betahistine and monoamine oxidase inhibitor interact in a synergistic manner. As used herein, the term "synergistic" means that betahistine and monoamine oxidase inhibitor produce a greater effect when used in combination than would be expected from adding the individual effects of the two components. Advantageously, a synergistic interaction may allow for lower doses of each component to be administered to a patient, thereby decreasing toxicity, whilst producing and/or maintaining the same therapeutic effect. Thus, in a particularly preferred embodiment, each component can be administered in a sub-therapeutic amount.

In another preferred embodiment, the betahistine and monoamine oxidase inhibitor produce a greater effect when used in combination than would be expected based on the effect of betahistine alone. Advantageously, the interaction between the betahistine and monoamine oxidase inhibitor allows for lower doses of betahistine to be administered to a patient, thereby decreasing toxicity, whilst producing and/or maintaining the same therapeutic effect.

Another aspect of the invention relates to a combination comprising (i) betahistine, or a pharmaceutically acceptable salt thereof, and (ii) a monoamine oxidase inhibitor, for use in treating or prevention one or more symptoms of vertigo in a subject. As used herein, the term "combination" refers to the actives being in a single formulation, or in separate formulations. Preferably, the actives are in separate formulations. Where the monoamine oxidase inhibitor (e.g. selegiline) and the betahistine or pharmaceutically acceptable salt thereof, are administered in the same formulation, preferably the dosage of monoamine oxidase inhibitor is low enough such that the total daily dosage does not exceed 5 mg per day. For example, in one particularly preferred embodiment, the formulation may comprise 24 mg betahistine and 0.5 mg of selegiline per unit dosage (or tablet).

Another aspect of the invention relates to the use of (i) betahistine, or a pharmaceutically acceptable salt thereof, and (ii) a monoamine oxidase inhibitor, in the preparation of a medicament for the treatment or prevention of one or more symptoms of vertigo.

Another aspect of the invention relates to the use of a monoamine oxidase inhibitor, or a pharmaceutically acceptable salt thereof, in the preparation of a medicament for the treatment or prevention of one or more symptoms of vertigo, wherein said medicament is for use in combination therapy with betahistine, or a pharmaceutically acceptable salt thereof.

Another aspect of the invention relates to the use of betahistine, or a pharmaceutically acceptable salt thereof, in the preparation of a medicament for the treatment or prevention of one or more symptoms of vertigo, wherein said medicament is for use in combination therapy with a monoamine oxidase inhibitor.

Another aspect of the invention relates to the use of betahistine, or a pharmaceutically acceptable salt thereof, in the preparation of a medicament for the treatment or prevention of one or more symptoms of vertigo, wherein said treatment comprises administering to a subject simultaneously, sequentially or separately a monoamine oxidase inhibitor, and betahistine, or a pharmaceutically acceptable salt thereof.

Another aspect of the invention relates to the use of a monoamine oxidase inhibitor in the preparation of a medicament for the treatment or prevention of one or more symptoms of vertigo, wherein said treatment comprises administering to a subject simultaneously, sequentially or separately betahistine, or a pharmaceutically acceptable salt thereof, and a monoamine oxidase inhibitor.

Another aspect of the invention relates to betahistine, or a pharmaceutically acceptable salt thereof, and a monoamine oxidase inhibitor as a combined preparation for simultaneous, sequential or separate use in treating or prevention of one or more symptoms of vertigo.

Another aspect of the invention relates to a method of treating or preventing one or more symptoms of vertigo in a subject, said method comprising administering to the subject (i) betahistine, or a pharmaceutically acceptable salt thereof, and (ii) a monoamine oxidase inhibitor.

Another preferred aspect of the invention relates to a method of treating Menière's disease in a subject, said method comprising administering to the subject (i) betahistine, or a pharmaceutically acceptable salt thereof, and (ii) a monoamine oxidase inhibitor.

Another preferred embodiment of the invention relates to a method of treating Menière's disease in a subject, said method comprising administering to a subject (i) betahistine, or a pharmaceutically acceptable salt thereof, and (ii) seleginine or a pharmaceutically acceptable salt thereof.

Betahistine

Betahistine is a histamine analogue known as 2-[2-(methylamino)ethyl]pyridine and having the structure shown below:

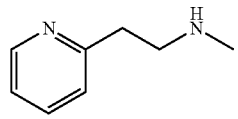

Betahistine is prescribed for the treatment of Menière's disease. It is typically formulated as the dihydrochloride salt and is available under the brand names Veserc, Serc, Hiserk, Betaserc and Vergo. Commonly supplied as a tablet for oral administration, each tablet typically contains between 8-24 mg of betahistine dihydrochloride, with a total daily dosage for adults between 24-48 mg per day, preferably divided into three equal doses.

Studies in an animal model [41] suggest that betahistine acts as strong H3 receptor antagonist, leading to vasodilation of the anterior inferior cerebellar artery and an increase in cochlear blood flow. It is thought that this increase in cochlear blood flow leads to greater resorption of endolymph into the subarachnoid space and a reduction in swelling of the membranous labyrinth [42], leading to a reduced frequency of attacks.

Whilst betahistine is approved for the treatment of Menière's disease in Europe, there is still insufficient evidence to demonstrate a therapeutically beneficial effect [43]. Accordingly, effective treatments for Menière's disease are still required.

Monoamine Oxidase Inhibitors

Monoamine oxidases (MAO) are a family of enzymes that catalyze the oxidative deamination of monoamines. They are found bound to the outer membrane of mitochondria in most cell types in the body and belong to the protein family of flavin-containing amine oxidoreductases. In humans there are two types of MAO: MAO-A and MAO-B. Both are found in neurons and astroglia. MAO-A is also found in the liver, pulmonary vascular endothelium, gastrointestinal tract, and placenta. MAO-B is mostly found in blood platelets.

Both MAOs are also vital to the inactivation of monoaminergic neurotransmitters, for which they display different specificities. Serotonin, melatonin, norepinephrine, and epinephrine are mainly broken down by MAO-A, whereas phenethylamine and benzylamine are mainly broken down by MAO-B. Both forms break down dopamine, tyramine, and tryptamine equally. In view of their role in the inactivation of neurotransmitters, MAO dysfunction is thought to be responsible for a number of psychiatric and neurological disorders. MAO-A inhibitors act as antidepressant and antianxiety agents, whereas MAO-B inhibitors are used alone or in combination to treat Alzheimer's and Parkinson's diseases.

Some MAO inhibitors inhibit both MAO-A and MAO-B equally, whereas others have been developed to target one over the other. Non-selective MAO-A/MAO-B inhibitors include the hydrazines Isocarboxazid (Marplan), Nialamide (Niamid), Phenelzine (Nardil, Nardelzine), Hydracarbazine, and the non-hydrazine Tranylcypromine (Parnate, Jatrosom). Other examples of non-selective MAO-A/MAO-B inhibitors include Benmoxin (Nerusil, Neuralex), Iproclozide (Sursum), Iproniazid (Marsilid, Iprozid, Ipronid, Rivivol, Propilniazida) (discontinued worldwide except for France), Mebanazine (Actomol), Octamoxin (Ximaol, Nimaol), Pheniprazine (Catron), Phenoxypropazine (Drazine), Pivalylbenzhydrazine (Tersavid), Safrazine (Safra) (discontinued worldwide except for Japan) and Caroxazone (Surodil, Timostenil).

In one highly preferred embodiment, the monamine oxidase inhibitor is a MAO-A inhibitor. Examples of MAO-A inhibitors include, but are not limited to, Bifemelane (Alnert, Celeport; available in Japan), Moclobemide (Aurorix, Manerix), Pirlindole (Pirazidol; available in Russia), Toloxatone (Humoryl; available in France) and Minaprine (Cantor).

In another highly preferred embodiment, the monamine oxidase inhibitor is a MAO-B inhibitor. Examples of MAO-B inhibitors include, but are not limited to, selegiline and rasagiline.

Standard laboratory assays can be used to determine whether a compound is a MAO-A or MAO-B inhibitor (e.g. Monoamine Oxidase Assay Kit available from Sigma Aldrich, which is a fluorimetric assay; or Cyprotex Monoamine Oxidase Assay Kit).

Selegiline

In one highly preferred embodiment, the monamine oxidase-B inhibitor is selegiline, or a pharmaceutically acceptable salt thereof. More preferably, the monamine oxidase-B inhibitor is selegiline hydrochloride.

Selegiline (also known as L-deprenyl), is a substituted phenethylamine known as N-methyl-N-(2-propynyl)-2-methyl-1-phenylethyl-2-amine and having the structure shown below:

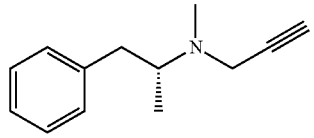

Selegiline

Selegiline is an irreversible MOA-B inhibitor prescribed for the treatment of Parkinson's disease, often in combination with L-dopa [53, 54]. Selegiline also inhibits MOA-A at certain doses. A transdermal patch (brand name, Emsam) is used to treat depression. To date, selegiline has not been disclosed as being therapeutically useful in the treatment of Menière's disease, either alone or in combination with any other active agent.

Selegiline's ability to inhibit MOA-B has rendered it a useful agent in the treatment of Parkinson's disease. When used alone, in the early stages of Parkinson's disease, selegiline exerts a mild beneficial therapeutic effect and delays the need for L-Dopa therapy. When used in combination with L-Dopa, selegiline potentiates the effects of L-Dopa and allows for a reduction in the required daily dosage, leading to fewer L-Dopa associated side effects. In addition to its MOA-B inhibitory activity, selegiline has recently been shown in vitro [44] to delay α-synuclein fibril formation by inhibiting initial nuclei formation and to a lesser extent, subsequent fibril elongation.

Betahistine Pretreatment

In one embodiment, the subject is treatment naive, i.e has not received prior treatment with betahistine. In another embodiment, the presently claimed combination therapy is particularly effective in subjects that have previously received betahistine monotherapy, for example, subjects where administering treatment with betahistine alone has proved therapeutically ineffective, or where the subject requires extremely high daily doses of the drug for it to have a therapeutically significant effect.

In one preferred embodiment, the subject has been previously treated (pretreated) with betahistine, or a pharmaceutically acceptable salt thereof.

As used herein, a "therapeutically significant effect" refers to the subject being free of attacks (e.g. vertigo symptoms associated with Menière's disease) for a specific period of time, for example, at least three months.

As used herein, "betahistine monotherapy" refers to treatment with betahistine, or a pharmaceutically acceptable salt thereof, in the absence of selegiline, or a pharmaceutically acceptable salt thereof. Preferably, the betahistine is administered in the absence of any other active agent.

As used herein, the term "pretreated" means that the subject has received monotherapy with betahistine, or a pharmaceutically acceptable salt thereof, for a period of time prior to commencement of combination therapy.

More preferably, the subject has received betahistine, or a pharmaceutically acceptable salt thereof, for a period of at least 6 months, more preferably, at least 12 months prior to commencement of combination therapy. During this pretreatment period, the subject's response to monotherapy with betahistine can be evaluated, including the optimal daily dose required to achieve a therapeutically significant effect.

Betahistine monotherapy is approved in Europe for treatment of Menière's syndrome, the symptoms of which include vertigo, tinnitus, hearing loss and nausea. According to the Summary of Product Characteristics, the maximum dose is 48 mg per day. However, recent clinical studies have indicated that this dose, and indeed higher doses (48 mg three times a day), are not effective in the treatment of Menière's disease [39,40].

In one preferred embodiment, the subject has been previously treated with betahistine monotherapy for a period of at least 12 months, but a therapeutically significant effect has not been achieved, i.e. the subject has not been free of attacks of Menière's disease symptoms for at least three months.

In one preferred embodiment, the subject has received betahistine, or a pharmaceutically acceptable salt thereof, for a period of at least 12 months prior to the start of the combination therapy, in an amount of greater than 48 mg per day.

In another preferred embodiment, the subject has received betahistine, or a pharmaceutically acceptable salt thereof, for a period of at least 12 months prior to the start of the combination therapy, in an amount of greater than 120 mg per day.

In another preferred embodiment, the subject has received betahistine, or a pharmaceutically acceptable salt thereof, for a period of at least 12 months prior to the start of the combination therapy, in an amount of greater than 240 mg per day.

In another preferred embodiment, the subject has received betahistine, or a pharmaceutically acceptable salt thereof, for a period of at least 12 months prior to the start of the combination therapy, in an amount of greater than 480 mg per day.

In some instances, studies by the Applicant have indicated that subjects require at least 20 tablets per day (24 mg betahistine per tablet), in some cases even more (for example, from 40 to 60 and even 80×24 mg tablets per day), in order to observe a therapeutically significant effect with betahistine monotherapy. These subjects are particularly suitable for subsequent combination therapy with betahistine and a monoamine oxidase inhibitor such as selegiline. Using the presently claimed combination treatment, the daily dosage of betahistine can be significantly reduced, for example, to as few as 18×24 mg tablets per day, or 12×24 mg tablets per day, or even as few as 3×24 mg tablets per day.

Salts

The agents of the present invention can be present as salts, in particular pharmaceutically acceptable salts or esters.

Pharmaceutically acceptable salts of the agents of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

In one preferred embodiment, the betahistine is in the form of betahistine dihydrochloride.

In another preferred embodiment, the betahistine is in the form of betahistine mesylate.

In one preferred embodiment, the selegiline is in the form of selegiline hydrochloride.

Pharmaceutical Carriers, Excipients or Diluents

The actives of the present combination are typically administered in admixture with a pharmaceutical carrier, excipient or diluent, particularly for human therapy. Examples of such suitable excipients for the various different forms of pharmaceutical compositions described herein may be found in the "Handbook of Pharmaceutical Excipients, $2^{nd}$ Edition, (1994), Edited by A Wade and P J Weller. Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Enantiomers/Tautomers

The invention also includes where appropriate all enantiomers and tautomers of the agents. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the agents of the present invention. The terms used in the claims encompass these forms.

Polymorphs

The invention furthermore relates to agents of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes agents of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

Preferably, the monoamine oxidase inhibitor (e.g. selegiline), or pharmaceutically acceptable salt thereof, is formulated for oral administration.

Preferably, the betahistine, or pharmaceutically acceptable salt thereof, is formulated for oral administration.

For oral administration, particular use is made of compressed tablets, pills, tablets, gellules, drops, and capsules. Preferably, these compositions contain from 1 to 2000 mg and more preferably from 50-1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

In one preferred embodiment, the betahistine, or pharmaceutically acceptable salt thereof, is administered orally, preferably in tablet form.

In one preferred embodiment, the monoamine oxidase inhibitor (e.g. selegiline, or pharmaceutically acceptable salt thereof), is administered orally, preferably in tablet form.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Dosages and frequency of application are typically adapted to the general medical condition of the patient and to the severity of the adverse effects caused, in particular to those caused to the hematopoietic, hepatic and to the renal system. The total daily dose can be administered as a single dose or divided into separate dosages administered two, three or four time a day.

In one preferred embodiment, the betahistine or pharmaceutically acceptable salt thereof is administered in an amount of from about 50 to about 900 mg per day, preferably from about 50 to about 500 mg per day, even more preferably, from about 50 to about 300 mg per day, more preferably from about 100 to about 300, or about 100 to about 200 mg per day.

In a more preferred embodiment, the betahistine or pharmaceutically acceptable salt thereof is administered in an amount of from about 70 to about 290 mg per day. In one embodiment, the total daily dose is from about 72 to about 864 mg (e.g. from 3 to 36×24 mg tablets). Preferably, the total daily dose is from about 72 to about 432 mg (e.g. from 3 to 18×24 mg tablets). More preferably, the total daily dose is from about 72 to about 288 mg (e.g. from 3 to 12×24 mg tablets). In another embodiment, the total daily dose is from about 72 to about 144 mg (e.g. from 3 to 6×24 mg tablets), or from about 72 to about 216 mg (e.g. from 3 to 9×24 mg tablets), or or from about 72 to about 360 mg (e.g. from 3 to 15×24 mg tablets), or from about 72 to about 576 mg (e.g. from 3 to 24×24 mg tablets), or from about 72 to about 720 mg (e.g. from 3 to 30×24 mg tablets). In another preferred embodiment, the total daily dose is no greater than 432 mg. In another preferred embodiment, the total daily dose is no greater than 288 mg per day.

In one preferred embodiment, the betahistine or pharmaceutically acceptable salt thereof is administered once, twice or three times a day. More preferably, the betahistine or pharmaceutically acceptable salt thereof is administered three times a day, for example, morning, lunchtime and night time.

In one preferred embodiment, the betahistine or pharmaceutically acceptable salt thereof is administered in unit dosage form.

In one preferred embodiment, the unit dosage comprises a 24 mg tablet of betahistine dihydrochloride, wherein from 3 to 18 tablets are administered per day, or 3 to 12, or 3 to 10, or 3 to 8, or 3 to 6 tablets per day.

The skilled person would understand that other unit dosages could also be used with the number of tablets adjusted accordingly to give equivalent daily dosages to those described herein.

In another preferred embodiment, the unit dosage comprises a 24 mg tablet of betahistine dihydrochloride, wherein from 4 to 18 tablets are administered per day, or 5 to 15, or 6 to 12, or 6 to 8, or 8 to 10 tablets per day.

In one preferred embodiment, the unit dosage comprises a 24 mg tablet of betahistine dihydrochloride, wherein from 3 to 36 tablets are administered per day, more preferably from 3 to 30, or from 3 to 24 tablets per day.

In one particularly preferred embodiment, the unit dosage comprises a 24 mg tablet of betahistine dihydrochloride, wherein from 3 to 12 tablets are administered per day.

In one preferred embodiment, the unit dosage comprises a 24 mg tablet of betahistine dihydrochloride, wherein 3 tablets are administered per day.

In another preferred embodiment, the unit dosage comprises a 24 mg tablet of betahistine dihydrochloride, wherein 6 tablets are administered per day.

In another preferred embodiment, the unit dosage comprises a 24 mg tablet of betahistine dihydrochloride, wherein 9 tablets are administered per day.

In another preferred embodiment, the unit dosage comprises a 24 mg tablet of betahistine dihydrochloride, wherein 12 tablets are administered per day.

In another preferred embodiment, the unit dosage comprises a 24 mg tablet of betahistine dihydrochloride, wherein 15 tablets are administered per day.

In another preferred embodiment, the unit dosage comprises a 24 mg tablet of betahistine dihydrochloride, wherein 18 tablets are administered per day.

In another preferred embodiment, the unit dosage comprises a 24 mg tablet of betahistine dihydrochloride, wherein 24 tablets are administered per day.

In another preferred embodiment, the unit dosage comprises a 24 mg tablet of betahistine dihydrochloride, wherein 30 tablets are administered per day.

In another preferred embodiment, the unit dosage comprises a 24 mg tablet of betahistine dihydrochloride, wherein 36 tablets are administered per day.

In one particularly preferred embodiment, the betahistine or pharmaceutically acceptable salt thereof is administered in a total daily dosage of no greater than 36×24 mg tablets, i.e. no greater than 864 mg per day.

In one particularly preferred embodiment, the betahistine or pharmaceutically acceptable salt thereof is administered in a total daily dosage of no greater than 18×24 mg tablets, i.e. no greater than 432 mg per day.

In one particularly preferred embodiment, the betahistine or pharmaceutically acceptable salt thereof is administered in a total daily dosage of no greater than 12×24 mg tablets, i.e. no greater than 288 mg per day.

In one particularly preferred embodiment, the betahistine or pharmaceutically acceptable salt thereof is administered in a total daily dosage of no greater than 15×24 mg tablets, i.e. no greater than 360 mg per day.

In one particularly preferred embodiment, the betahistine or pharmaceutically acceptable salt thereof is administered in a total daily dosage of no greater than 24×24 mg tablets, i.e. no greater than 576 mg per day.

In one particularly preferred embodiment, the betahistine or pharmaceutically acceptable salt thereof is administered in a total daily dosage of no greater than 30×24 mg tablets, i.e. no greater than 720 mg per day.

In one preferred embodiment, the monoamine oxidase inhibitor or pharmaceutically acceptable salt thereof is administered in an amount of from about 1 to about 15 mg per day, more preferably, about 1.25 to about 10 mg/day.

In one preferred embodiment, the monoamine oxidase inhibitor or pharmaceutically acceptable salt thereof is administered in an amount of about 5 to about 10 mg per day. In one highly preferred embodiment, the selegiline or pharmaceutically acceptable salt thereof is administered in an amount of about 5 mg per day.

In one preferred embodiment, the selegiline or pharmaceutically acceptable salt thereof is administered in an amount of from about 1 to about 15 mg per day, more preferably, about 1.25 to about 10 mg/day.

In one preferred embodiment, the selegiline or pharmaceutically acceptable salt thereof is administered in an amount of about 5 to about 10 mg per day. In one highly preferred embodiment, the selegiline or pharmaceutically acceptable salt thereof is administered in an amount of about 5 mg per day.

In one preferred embodiment, the unit dosage comprises a 5 mg tablet of selegiline hydrochloride.

In one preferred embodiment, the selegiline or pharmaceutically acceptable salt thereof is administered once a day, for example, one 5 mg tablet per day.

In another preferred embodiment, the selegiline or pharmaceutically acceptable salt thereof is administered twice a day, for example, half a 5 mg tablet twice a day.

In another preferred embodiment, the selegiline or pharmaceutically acceptable salt thereof is administered once a day, for example, two 5 mg tablets once a day. In another preferred embodiment, the selegiline or pharmaceutically acceptable salt thereof is administered twice a day, for example, one 5 mg tablet twice a day.

Advantageously, administering the selegiline, or pharmaceutically acceptable salt thereof, in two daily doses can lead to a reduction in certain side effects, such as transient fullness of head or headaches due to vasodilation. Preferably, where the selegiline, or pharmaceutically acceptable salt thereof, is administered twice a day, half a tablet is taken in the morning, and half a tablet is taken at night.

In another preferred embodiment, the selegiline or pharmaceutically acceptable salt thereof is administered in a total daily dose of no more than 5 mg per day.

BRIEF DESCRIPTION OF DRAWING

The present invention is further described by way of the following non-limiting examples and FIGURES, wherein:

FIG. 1 shows the daily dosage of betahistine-dihydrochloride (mg) with and without selegiline taken by 13 patients with Menière's disease (MD) during a monotherapy (left) and during the combined therapy with 5 mg/d selegiline to respond to the treatment defined by ≤1 attack per three months. The thick black line indicates the mean dosage of betahistine per day of the 13 patients. There was a significant reduction from 895.4 to 204.0 per day (mean, p<0.001, paired t-test).

EXAMPLES

Materials and Methods

Betahistine dihydrochloride tablets were obtained from Abbott (Vasomotol 24 mg tablets). Selegiline hydrochloride tablets were obtained from Hexal.

Study Design

Studies by the Applicant investigated the benefits of a high-dosage betahistine monotherapy compared with those of a lower dosage of betahistine in combination with the MAO B inhibitor (MAO-B) selegiline on the frequency of acute attacks of vertigo in patients with Menière's disease (MD).

More specifically, studies investigated the effect of combination therapy in 13 subjects receiving 5 mg per day selegiline hydrochloride (either as one tablet at night, or half a tablet in the morning and half a tablet at night), in conjunction with varying amounts of betahistine dihydrochloride per day (amounts ranging from n=3 to 36, where n is the number of 24 mg tablets per day). All subjects had previously received treatment with betahistine dihydrochloride monotherapy (in amounts ranging from n=9 to 80, where n is the number of 24 mg tablets per day), and the number of vertigo attacks per month were recorded during a three month period of monotherapy prior to commencement of combination treatment. Following combination treatment, the subjects then recorded the number of vertigo attacks per month during the last two months of combination treatment.

The 13 patients in this observational study fulfilled the current diagnostic criteria of MD [48]. Patients with the diagnosis of other peripheral or central vestibular disorders, such as vestibular migraine, benign paroxysmal positional vertigo, paroxysmal brainstem attacks, or functional dizziness, were not included. Patients suffering from known contraindications or hypersensitivity to betahistine, such as bronchial asthma, pheochromocytoma, or treatment with other antihistaminic drugs, ulcer of the stomach or duodenum, or severe dysfunction of liver or kidney were also not treated with betahistine. Patients with known contraindications (e.g., use of meperidine or other opioids, tricyclic antidepressants or non-selective MAOIs, selective serotonin re-uptake inhibitors) or hypersensitivity to selegiline were not treated with this agent [51].

Based on the results of the BEMED trial (showing that betahistine 48 mg tid is evidently not effective) the study initially started with a dosage of 96 mg tid in all patients. During the three- to six-monthly follow-up examinations the daily dosages were adjusted according to the patient's response (approach: "titration" of attacks of vertigo). Patients had been treated for at least 18 months with high dosages of betahistine-dihydrochloride and had ≤1 attacks for at least three months.

An initial dosage of 5 mg/day selegiline hydrochloride was chosen (approved dosage for Parkinson's disease is 5 to 10 mg/d). In parallel the dosage of betahistine was reduced to about a tenth of the initial dosage. The design of the observational study was approved by the local ethics committee. Follow-up examinations were after 1 month and then every 3 months to check the efficacy of the treatment and the side-effects and to adjust the betahistine dosage if necessary. Ideally, the objective was to achieve ≤1 attack per three months.

Preliminary Results

Patient characteristics were as follows: n=13, 7 females, 6 males; age range 40 to 75 yrs; mean age 58.9 yrs. Further details are shown in Table 1.

Based on the negative results of the BEMED trial, the patients started on a dosage of betahistine of 96 mg tid. Then the dosage was adjusted according to the number of attacks of vertigo per three months. The daily betahistine-dihydrochloride dosage eventually required to achieve a treatment response (≤1 attack for three months) ranged from 216 to 1920 mg (mean 895.4 mg/d, FIG. 1), i.e. 9 to 80 24-mg tablets per day (mean 37.3). This was well tolerated except for some fullness of the stomach in 4 patients which responded well to the proton-pump inhibitor pantoprazole (20 to 40 mg per day).

After informing the patients that theoretically the betahistine dosage can be reduced when a patient also takes selegiline, the dosage was first reduced to about 10% of the initial dosage for three months. Finally, after the combination with 5 mg/d selegiline, the dosage needed to achieve the same benefit for at least three months was 3 to 36 24-mg tablets (mean 8.5), i.e. 72 to 864 mg/d (mean 204.9 mg/d, p<0.001, paired t-test). One patient transiently stopped the treatment with selegiline, another one reduced the dosage to 2.5 mg per day and the attacks re-occurred after 2 to 4 weeks. Six out of 13 patients reported transient fullness of the head or too much blood in the head during the combined treatment; in two of them this disappeared when switching to selegiline 2.5 mg bid.

Of the 13 subjects tested, 10 were completely free from vertigo attacks during the last four months of combination treatment. One patient suffered only 1 vertigo attack per month during the last two months of combination treatment. Two patients suffered only one attack during the last 3 months of combination treatment. One subject also noted an improvement in tinnitus symptoms. Four subjects commented that they were very happy with the treatment. Other side effects included slight nausea (1 subject).

In the longer term (>9 months), one patient had to increase the selegiline dosage to 5 mg twice per day because the attacks had re-occurred (up to three attacks per month); after increasing the selegiline dosage they experienced ≤1 attack per month. Eleven patients are still on selegiline treatment (5 mg per day), one is on 2.5 mg selegiline per day, one patient stopped selegiline because they were free of attacks for more than six months.

The major finding of this observational study in 13 patients is that the combination of a lower dosage of betahistine and the MAO inhibitor selegiline (5 mg/d) has the same benefit as very high dosages of betahistine (of up to 1920 mg/d). This benefit can be explained by an increase of the blood concentrations of betahistine due to reduction of the normally almost complete first-pass effect (99%) of betahistine, leading to plasma concentrations of less than 0.5 ng/ml [52].

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

REFERENCES

1. Minor L B, Schessel D A, Carey J P. Menière's disease. *Curr Opin Neurol* 2004; 17: 9-16. doi:10.1097/00019052-200402000-00004
2. Hallpike C S, Cairns H. Observations on the Pathology of Menière's Syndrome: (Section of Otology). *Proc R Soc Med* 1938; 31: 1317-36.
3. Gürkov R, Flatz W, Louza J, Strupp M, Krause E. In vivo visualization of endolyphatic hydrops in patients with Menière's disease: correlation with audiovestibular function. *Eur Arch Otorhinolaryngol* 2011; 268: 1743-8. doi: 10.1007/s00405-011-1573-3
4. Harris J P, Alexander T H. Current-day prevalence of Menière's syndrome. *Audiol Neurootol* 2010; 15: 318-22. doi:10.1159/000286213
5. Alexander T H, Harris J P. Current epidemiology of Menière's syndrome. *Otolaryngol Clin North Am* 2010; 43: 965-70. doi:10.1016/j.otc.2010.05.001
6. Wladislavosky-Waserman P, Facer G W, Mokri B, Kurland L T. Menière's disease: a 30-year epidemiologic and clinical study in Rochester, Minn., 1951-1980. *Laryngoscope* 1984; 94: 1098-102.
Paparella M M, Mancini F. Vestibular Menière's disease. *Otolaryngol Head Neck Surg* 1985; 93: 148-51.
8. Thirlwall A S, Kundu S. Diuretics for Menière's disease or syndrome. *Cochrane Database Syst Rev* 2006; 3: CD003599.
9. Fisher L M, Derebery M J, Friedman R A. Oral steroid treatment for hearing improvement in Menière's disease and endolymphatic hydrops. *Otol Neurotol* 2012; 33: 1685-91. doi:10.1097/MAO.0b013e31826dba83
10. Phillips J S, Westerberg B. Intratympanic steroids for Menière's disease or syndrome. *Cochrane Database Syst Rev* 2011; 7: CD008514.
11. Watanabe Y, Shojaku H, Junicho M et al. Intermittent pressure therapy of intractable Menière's disease and delayed endolymphatic hydrops using the transtympanic membrane massage device: a preliminary report. *Acta Otolaryngol* 2011; 131: 1178-86. doi:10.3109/00016489.2011.600331
12. Park J J, Chen Y S, Westhofen M. Menière's disease and middle ear pressure: vestibular function after transtympanic tube placement. *Acta Otolaryngol* 2009; 129: 1408-13.doi:10.3109/00016480902791678
13. Yu M S, Lee K S, Chung J W. Long-term results of endolymphatic mastoid shunt surgery in patients with intractable Menière's disease. *Otolaryngol Head Neck Surg* 2009; 141: 237-42. doi:10.1016/j.otohns.2009.03.014
14. Barbara M, Lazzarino A I, Biagini M, Costa M, Monini S. Influence of Meniett® treatment on hearing. *Acta Otolaryngol* 2010; 130: 1256-9. doi:10.3109/00016481003782033
15. Gürkov R, Filipe Mingas L B, Rader T, Louza J, Olzowy B, Krause E. Effect of transtympanic low-pressure therapy in patients with unilateral Menière's disease unresponsive to betahistine: a randomised, placebo-controlled, double-blinded, clinical trial. *J Laryngol Otol* 2012; 126: 356-62. doi:10.1017/S0022215112000102
16. Ahsan S F, Standring R, Wang Y. Systematic review and meta-analysis of Meniett therapy for Menière's disease. *Laryngoscope* 2015; 125:203-8. doi:10.1002/lary.24773
17. van Sonsbeek S, Pullens B, van Benthem P P. Positive pressure therapy for Menière's disease or syndrome. *Cochrane Database Syst Rev* 2015; 3: CD008419.
18. Pullens B, van Benthem P P. Intratympanic gentamicin for Menière's disease or syndrome. *Cochrane Database Syst Rev* 2011; 3: CD008234.
19. Wasson J, Upile N, Pfleiderer A. Intratympanic gentamicin treatment for unilateral Menière's disease: long-term follow up of a proven regime. *J Laryngol Otol* 2013; 127: 20-4. doi:10.1017/S0022215112002605

20. Goto F, Tsutsumi T, Ogawa K. Lateral semicircular canal plugging with endolymphatic sac decompression as new surgical treatment for intractable Menière's disease. *Acta Otolaryngol* 2012; 132: 893-5.
21. Huang T S. Endolymphatic sac surgery for Menière's disease: experience with over 3000 cases. *Otolaryngol Clin North Am* 2002; 35: 591-606. doi:10.1016/S0030-6665(02)00027-0
22. Teufert K B, Doherty J. Endolymphatic sac shunt, labyrinthectomy, and vestibular nerve section in Menière's disease. *Otolaryngol Clin North Am* 2010; 43: 1091-111. doi:10.1016/j.otc.2010.05.014
23. Cutler A R, Kaloostian S W, Ishiyama A, Frazee J G. Two-handed endoscopic-directed vestibular nerve sectioning: case series and review of the literature. *J Neurosurg* 2012; 117: 507-13. doi:10.3171/2012.6.JNS111818
24. Harner S G, Driscoll C L, Facer G W, Beatty C W, McDonald T J. Long-term follow-up of transtympanic gentamicin for Menière's syndrome. *Otol Neurotol* 2001; 22: 210-4. doi:10.1097/00129492-200103000-00016
25. Pullens B, Verschuur H P, van Benthem P P. Surgery for Menière's disease. *Cochrane Database Syst Rev* 2013; 2: CD005395.
26. Lacour M. Betahistine treatment in managing vertigo and improving vestibular compensation: clarification. *J Vestib Res* 2013; 23: 139-51.
27. Ihler F, Bertlich M, Sharaf K, Strieth S, Strupp M, Canis M. Betahistine exerts a dose-dependent effect on cochlear stria vascularis blood flow in guinea pigs in vivo. *PLoS One* 2012; 7: e39086. doi:10.1371/journal.pone.0039086
28. Bertlich M, Ihler F, Freytag S, Weiss B G, Strupp M, Canis M. Histaminergic H3-Heteroreceptors as a Potential Mediator of Betahistine-Induced Increase in Cochlear Blood Flow. *Audiol Neurootol* 2015; 20: 283-93. doi: 10.1159/000368293
29. Bertlich M, Ihler F, Sharaf K, Weiss B G, Strupp M, Canis M. Betahistine metabolites, aminoethylpyridine, and hydroxyethylpyridine increase cochlear blood flow in guinea pigs in vivo. *Int J Audiol* 2014; 53: 753-9. doi: 10.3109/14992027.2014.917208
30. Westhofen M. [Menière's disease: evidence and controversies]. *HNO* 2009; 57: 446-54. doi:10.1007/s00106-009-1915-2
31. Harcourt J, Barraclough K, Bronstein A M. Menière's disease. *BMJ* 2014; 349: g6544. doi:10.1136/bmj.g6544
32. Smith W K, Sankar V, Pfleiderer A G. A national survey amongst UK otolaryngologists regarding the treatment of Mèniere's disease. *J Laryngol Otol* 2005; 119: 102-5. doi:10.1258/0022215053419871
33. James A L, Burton M J. Betahistine for Menière's disease or syndrome. *Cochrane Database Syst Rev* 2001; 1: CD001873.
34. Nauta J J. Meta-analysis of clinical studies with betahistine in Mèniere's disease and vestibular vertigo. *Eur Arch Otorhinolaryngol* 2014; 271:887-97. doi:10.1007/500405-013-2596-8
35. Mira E, Guidetti G, Ghilardi L et al. Betahistine dihydrochloride in the treatment of peripheral vestibular vertigo. *Eur Arch Otorhinolaryngol* 2003; 260: 73-7.
36. Strupp M, Hupert D, Frenzel C et al. Long-term prophylactic treatment of attacks of vertigo in Menière's disease—comparison of a high with a low dosage of betahistine in an open trial. *Acta Otolaryngol* 2008; 128: 520-4. doi:10.1080/00016480701724912
37. Lezius F, Adrion C, Mansmann U, Jahn K, Strupp M. High-dosage betahistine dihydrochloride between 288 and 480 mg/day in patients with severe Menière's disease: a case series. *Eur Arch Otorhinolaryngol* 2011; 268: 1237-40. doi:10.1007/s00405-011-1647-2.
38. Committee for Medicinal Products for Human Use. *Guideline on clinical investigation of medicinal products for the treatment of migraine.* CPMP/EWP/788/2001 rev 1. European Medicines Agency, CHMP, 2007.
39. Adrion C, Simone Fischer C, Wagner J, Gurkov R, Mansmann U, Strupp M, Efficacy and safety of betahistine treatment in patients with Menière's disease: primary results of a long term, multicentre, double blind, randomised, placebo controlled, dose defining trial (BEMED trial); BMJ, 2016, 352; H6816/doi: 10.1136).
40. Harcourt J, Betahistine for Menière's Disease; Editorial; BMJ 2016; 352; i46 doi.10.1136).
41. E Laurikainen et al., *Eur. Arch. Otorhinolaryngol.,* 1998, 255, 119-123.
42. F Ihler et al., *PLOS ONE.,* 2012, 7(6), e39086.
43. J. A. Burton, *Cochrane Database of Systematic Reviews,* 2001, Issue 1. Art. No.: CD001873—updated 2011.
44. C. A Braga et al., J. Molec. Bio., 2011, 405, 254-273.
45. Murdin L, Hussain K, Schilder A G. Betahistine for symptoms of vertigo. Cochrane Database Syst Rev 2016; (6):CD010696.
46. Bisdorff A, Von Brevern M, Lempert T, Newman-Toker D E. Classification of vestibular symptoms: towards an international classification of vestibular disorders. *Journal of Vestibular Research: Equilibrium & Orientation* 2009; 19: 1-13.
47. Strupp M, Brandt T. Peripheral vestibular disorders. Current Opinion in Neurology 2013; 26:81-9.
48. Lopez-Escamez J A, Carey J, Chung W H, Goebel J A, Magnusson M, Mandalà M, et al. Diagnostic criteria for Menière's disease. *Journal of Vestibular Research* 2015; 25(1):1-7.
49. AAO-HNS. Committee on Hearing and Equilibrium guidelines for the diagnosis and evaluation of therapy in Menière's disease, American Academy of Otolaryngology—Head and Neck Foundation. Otolaryngology—Head and Neck Surgery 1995; 113:181-5.
50. Strupp M, Magnusson M. Acute Unilateral Vestibulopathy. Neurol Clin 2015; 33: 669-685.
51. NDA 20-647/S-006 and S-007; Eldepryl® (Selegiline hydrochloride) Capsules (see https://www.accessdata.fda-.gov/drugsatfda_docs/label/2008/020647s006s007lbl.pdf).
52. Chen X Y, Zhong D F, Duan J L, Yan B X (2003) LC-MS-MS analysis of 2-pyridylacetic acid, a major metabolite of betahistine: application to a pharmacokinetic study in healthy volunteers. Xenobiotica 33:1261-1271.
53. Dersi L, Vecsei L (2017) Monoamine oxidase B inhibitors in Parkinson's disease. CNS Neurol Disord Drug Targets.
54. Elsworth J D, Glover V, Reynolds G P, Sandler M, Lees A J, Phuapradit P, Shaw K M, Stern G M, Kumar P (1978) Deprenyl administration in man: a selective monoamine oxidase B inhibitor without the 'cheese effect'. Psychopharmacology (Berl) 57:33-38

TABLE 1

Clinical characteristics and dosages

| Patient | Sex, age, diagnosis | Dosage of betahistine (monotherapy) required that the patient had a significant effect before the combined treatment (n of 24-mg tablets) | Dosage of betahistine in combination with 5m selegiline (n of 24-mg tablets) |
|---|---|---|---|
| 1 | Female, 74 yrs, bilateral MD | 80 | 36 |
| 2 | Female, 69 yrs, MD, right | 30 | 3 |
| 3 | Female, 73 yrs, bilateral MD | 9 | 3 |
| 4 | Male, 43 yrs, bilateral MD | 36 | 6 |
| 5 | Female, 40 yrs, MD, right | 60 | 18 |
| 6 | Male, 51 yrs, bilateral MD | 24 | 3 |
| 7 | Male, 43 yrs, MD, left | 30 | 12 |
| 8 | Male, 52 yrs, MD, right | 18 | 3 |
| 9 | Male, 70 yrs, MD, right | 50 | 3 |
| 10 | Male, 57 yrs, bilateral MD | 40 | 6 |
| 11 | Male, 52 yrs, MD, left | 30 | 9 |
| 12 | Female, 67 yrs, MD, right | 18 | 3 |
| 13 | Female, 75 yrs, MD, left | 60 | 6 |

MD = Menière's Disease

The invention claimed is:

1. A method of treating or preventing one or more symptoms of vertigo in a subject, said method comprising administering to a subject an effective amount of a combination of:
   (i) a first active agent, which is betahistine, or a pharmaceutically acceptable salt thereof; and
   (ii) a second active agent, which is isocarboxazid, nialamide, phenelzine, hydracarbazine, tranylcypromine, benmoxin, iproclozide, iproniazid, mebanazine, octamoxin, pheniprazine, phenoxypropazine, pivalylbenhydrazine, safrazine, caroxazone, bifemelane, moclobemide, pirlindole, toloxatone, minaprine, or rasagiline, or a pharmaceutically acceptable salt of isocarboxazid, nialamide, phenelzine, hydracarbazine, tranylcypromine, benmoxin, iproclozide, iproniazid, mebanazine, octamoxin, pheniprazine, phenoxypropazine, pivalylbenhydrazine, safrazine, caroxazone, bifemelane, moclobemide, pirlindole, toloxatone, minaprine, or rasagiline.

2. The method according to claim 1, wherein the dosage of the first active agent in combination with the second active agent is reduced to about a third compared to the dosage of the first active agent administered in the absence of the second active agent.

3. The method according to claim 1, wherein the subject has been previously treated with the first active agent in the absence of the second active agent.

4. The method according to claim 3, wherein the subject has been previously treated with the first active agent in the absence of the second active agent for a period of at least 6 months.

5. The method of claim 1, wherein the amount of the first active agent administered is at least 48 mg per day.

6. The method of claim 1, wherein the first active agent is betahistine dihydrochloride or betahistine mesylate.

7. The method of claim 1, wherein the second active agent is rasagiline, or a pharmaceutically acceptable salt thereof.

8. The method of claim 1, wherein the first active agent is formulated for oral administration.

9. The method of claim 1, wherein the second active agent is formulated for oral administration.

10. The method of claim 1, wherein the first active agent is administered in an amount of from about 50 to about 900 mg per day.

11. The method of claim 1, wherein the first active agent is administered three times a day.

12. The method of claim 1, wherein the first active agent is administered in unit dosage form, wherein the unit dosage comprises a 24 mg tablet of betahistine dihydrochloride.

13. The method of claim 12, wherein administration of the first active agent is from 3 to 36 tablets per day.

14. The method of claim 13, wherein administration of the first active agent is from 3 to 12 tablets per day.

15. The method of claim 12, wherein administration of the first active agent in the absence of the second active agent is at least 2 tablets per day.

16. The method of claim 7, wherein the second active agent is administered in an amount of from about 1 to about 15 mg per day.

17. The method of claim 7, wherein the second active agent is administered at least once a day.

18. The method of claim 17, wherein the second active agent is administered twice a day.

19. The method of claim 1, wherein the vertigo is caused by, or associated with, Meniere's disease, vestibular neuritis, labyrinthitis, or benign paroxysmal positional vertigo.

20. The method of claim 1, wherein the administration of the first active agent and the second active agent occurs in a single formulation.

* * * * *